United States Patent [19]

Parker

[11] Patent Number: 4,735,905

[45] Date of Patent: Apr. 5, 1988

[54] SPECIMEN-GATHERING APPARATUS AND METHOD

[75] Inventor: James E. Parker, Long Beach, Calif.

[73] Assignee: V-Tech, Inc., Pomona, Calif.

[21] Appl. No.: 897,138

[22] Filed: Aug. 15, 1986

[51] Int. Cl.$^4$ .......................... G01N 1/00; B01L 3/00; B01L 9/00
[52] U.S. Cl. ..................................... 436/174; 422/99; 422/102; 422/104; 73/864.41; 73/864.51
[58] Field of Search .................... 422/99, 102, 104; 436/174; 73/864.14, 864.41, 864.51; 128/304, 749, 757, 759

[56] References Cited

U.S. PATENT DOCUMENTS

| | | | |
|---|---|---|---|
| 3,783,106 | 1/1974 | Henshilwood | 128/759 |
| 3,800,781 | 4/1974 | Zalucki | 128/749 |
| 3,857,384 | 12/1974 | Watson | 128/304 |
| 3,961,620 | 6/1976 | Schack et al. | 128/304 |
| 3,991,617 | 11/1976 | d'Autry | 73/864.14 |
| 4,353,868 | 10/1982 | Joslin et al. | 422/102 |

Primary Examiner—David L. Lacey
Assistant Examiner—Floyd E. Bennett, Jr.
Attorney, Agent, or Firm—Drucker & Sommers

[57] ABSTRACT

A specimen gathering method and apparatus having a piston operated ejectable scoop member. Preferably, the specimen gathering device inserts into a container and releasably seals the container. The apparatus is useful for gathering and transporting stool and other biological specimens.

15 Claims, 2 Drawing Sheets

U.S. Patent   Apr. 5, 1988   Sheet 1 of 2   4,735,905
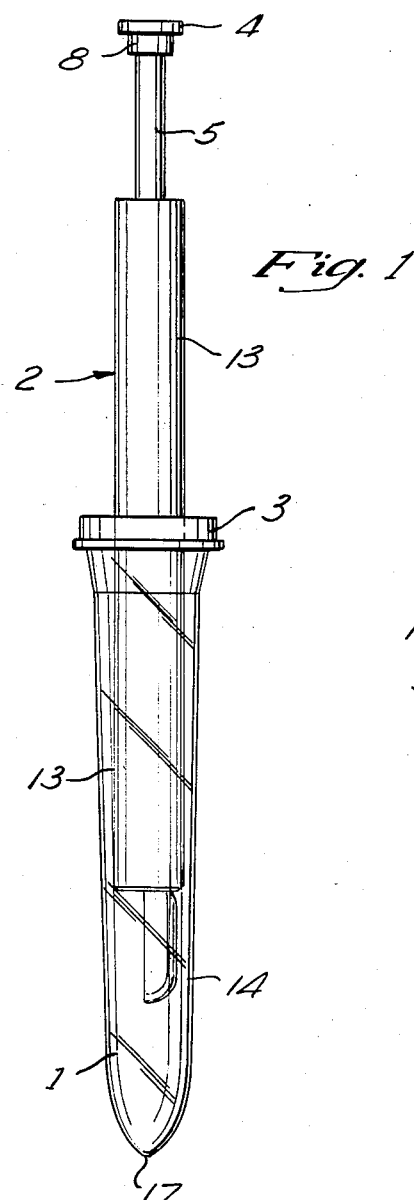
Fig. 1
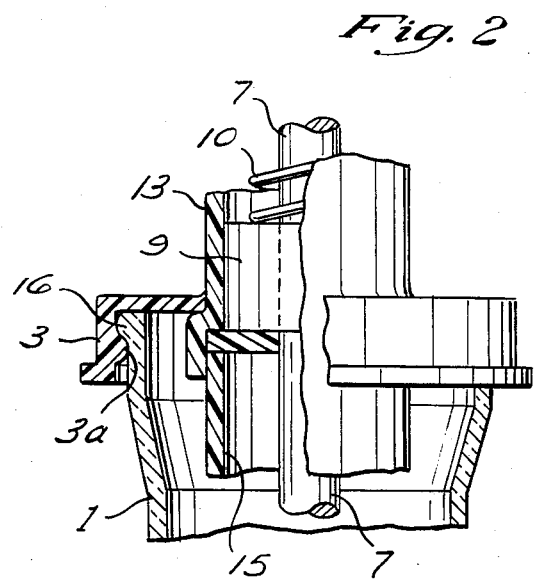
Fig. 2
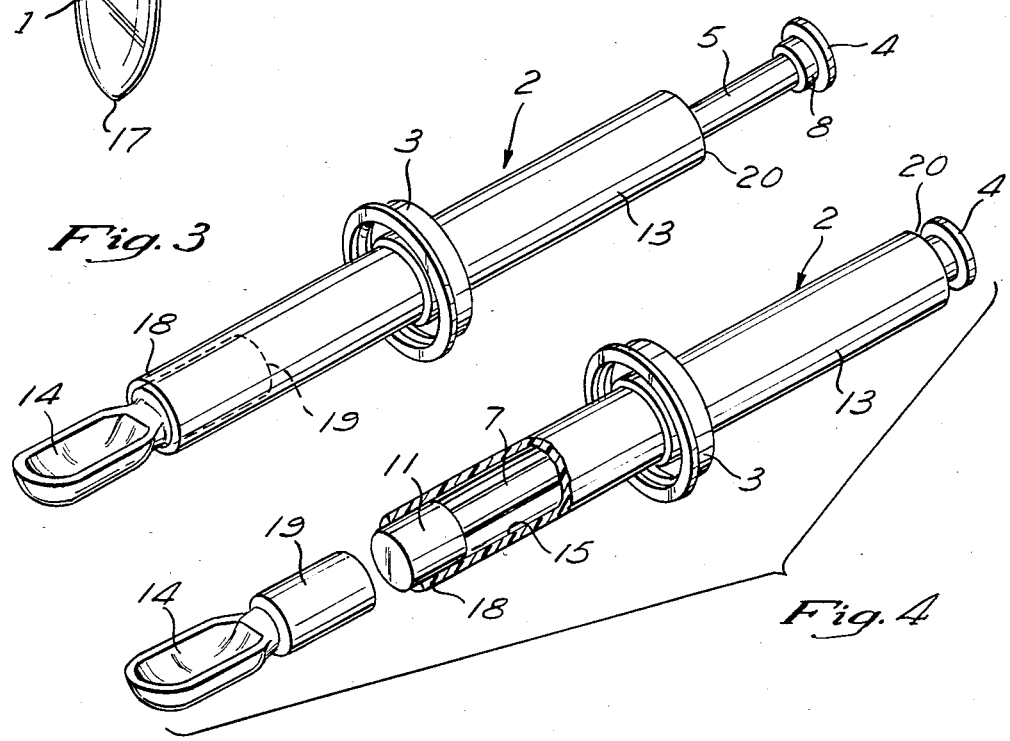
Fig. 3
Fig. 4

SPECIMEN-GATHERING APPARATUS AND METHOD

BRIEF DESCRIPTION OF THE INVENTION

1. Field of the Invention

This invention relates to a collecting method and apparatus for use by physicians, technicians, or patients for gathering and transporting specimens, and has particular use for collecting stool and other biological samples.

2. Prior Art

Numerous devices for the collection of stool and other samples are known, including toothpicks, spatulas, scrapers, and spoons. Some are combination collection and transport containers, wherein a spoon or spatula is attached to the inside of a container lid and thus is enclosed within the container when it is sealed for storage or shipment. This approach provides for simple and convenient sample collection, however, it also provides a risk of contamination of lab personnel by viruses, parasites, and other enteric pathogens when the container lid is opened or removed, through contact with the contaminated spoon attached to the lid.

Schack, et al. (U.S. Pat. No. 3,961,620) and Watson (U.S. Pat. No. 3,857,384) each show a more complicated cervical sampling apparatus including a housing and an extendable sampling member, however, the sampling member itself must be handled and examined in order to examine the specimen taken therewith.

There has long been a need in the art for convenient, efficient, and uncomplicated apparatus and method for collecting and transporting stool and other biological samples, while minimizing the risk of contamination of lab personnel and others handling the specimen.

There are other patents which involve specimen gathering devices and methods, but as far as the applicant is aware, the above-cited are the closest to the present invention.

BRIEF SUMMARY OF THE INVENTION

It is therefore an object of the invention to overcome some of the problems of the prior art by providing a method for gathering and transporting liquid, solid or mixed stool or other biological samples using a new apparatus having a container and a sampling device which is insertable into and seals the container. The novel sampling device has an ejectable specimen collecting scoop, which reduces the risk of contact and contamination by those handling the specimen.

DESCRIPTION OF THE DRAWINGS

FIG. 1 is an enlarged perspective view of the components of the apparatus of this invention showing their use in combination;

FIG. 2 is an enlarged, fragmentary, partly cross-sectional view of the middle of FIG. 1, showing a sampler positioned in a test tube;

FIG. 3 is a perspective view of a presently preferred embodiment of a sampler in its rest position;

FIG. 4 is a partly fragmentary, exploded, perspective view of the sampler of FIG. 3 in its compressed position, showing the ejected scoop member;

PREFERRED EMBODIMENT OF THE INVENTION

Figure 5:
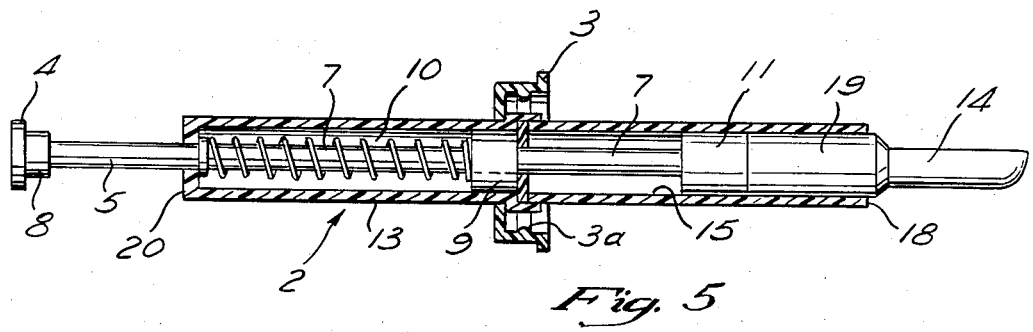
FIG. 5 is an enlarged, longitudinal cross-sectional view of one embodiment of the sampler of FIG. 3.

Referring to the drawings in this case, and especially FIG. 1, it may be seen that the apparatus of this invention is comprised of two components, namely, container or test tube 1, and sampler 2. Container 1 has open, upper end 16 and bottom end 17, and rigid walls. Container 1 may be provided with indicia (not shown) for measuring volumes therein. Container 1 may be initially provided with an amount of fixative or sample preservative, if desired.

Sampler 2 is provided with housing 13, having a bore 15 therethrough. As shown in FIGS. 1 and 2, sealing member 3 is provided on the outside of housing 13, and is designed to engage and seal the open upper end 16 of container 1. Sealing member 3 may be affixed to housing 13 by being molded in place, or by conventional methods such as adhesives. The seal member 3 is preferably provided with a shoulder 3a to enhance the seal between it and the upper end of the container 1.

Housing 13 is shown in the drawings, especially FIG. 2, as being made of two interlocking pieces. For ease of manufacture, it may be desirable to form housing 13 of a single, unitary construction. Alternatively, housing 13 may desirably be formed of two separate pieces which do not interfit, and are attached, by conventional means, to either side of sealing member 3.

Movable piston means 7 is affixed, for reciprocating movement, within housing 13. Piston means 7 has an enlarged forward or proximal end portion 11, located near end 18 of housing 13, and an enlarged piston rear or spring engagement member 12.

Figure 6:
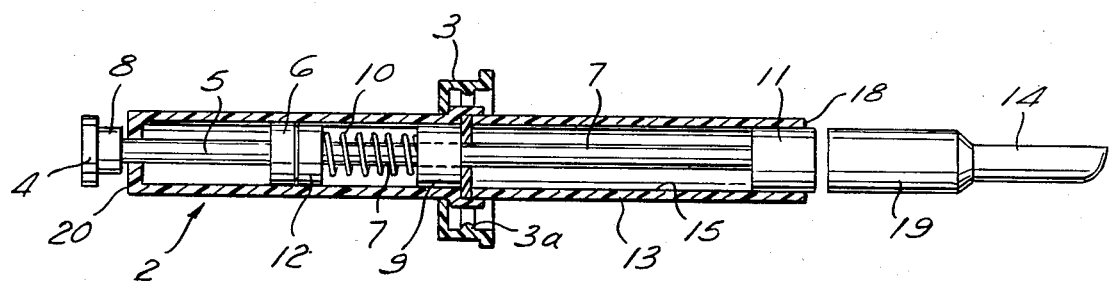
FIG. 6 is an enlarged, longitudinal cross-sectional view of another embodiment of the sampler of FIG. 3 in its compressed position.

Referring to FIG. 6, spring compression member 9 has a bore therethrough, and is positioned around piston means 7, intermediate piston end portions 11 and 12, and permits free reciprocating movement of piston means 7. Spring compression member 9 is sized to be wedge-fit into housing 13, but may instead by affixed thereto by suitable conventional adhesives.

Spring 10 is provided around piston means 7, intermediate spring compression member 9 and spring engagement member 12 of piston means 7. It is presently preferred that spring 10 be fabricated of suitable metal.

As shown particularly in FIG. 6, piston means 7 is operated by push rod 5, placed partly within and partly beyond housing 13. Push rod forward or proximal end portion 6 abuts piston means opening engagement member 12, and is enlarged with respect to the remainder of push rod 5.

In another embodiment, FIG. 5, piston means 7 and push rod 5 are of unitary construction, so that push rod proximal end portion 6 and piston means spring engagement member 12 are integrally affixed by suitable conventional adhesives, or by being molded in place.

The bore 15 through rear housing end 20 is narrower than through the remainder of housing 13, and is sized to prevent the passage of push rod proximal end portion 6 therethrough. The distal end 8 of push rod 6 is provided with push rod handle means 4.

Insert end 19 of specimen gathering scoop member 14 is positioned inside end 18 of housing 13 and is dimensioned for slidable movement within the bore 15, so that scoop member 14 is readily removable from housing 13 upon movement of insert end 19—under the influence of member 11 attached to piston means 7 (see FIG. 6). The shape of scoop member 14 may be varied from that shown in the figures to suit different samples, and may, for example, be flattened like a spatula, or provided with a deeper scoop than shown.

All components described above can be fabricated at relatively high production rates using inexpensive material, and thus are particularly suited as single-use disposable items. The embodiments of samplers and containers, above described, can be conveniently molded using any number of suitable plastics.

The method of use of the apparatus is as follows:

An amount of stool or other biological specimen is collected in a collection container (such as a cone-shaped paper cup) (not shown). The technician, patient, or other operator grasps sampler 2 near end 20 of housing 13, placing thumb or index finger on push rod handle means 4, leaving piston means 7 in its normally uppermost rest position, shown in FIG. 3.

A portion of the specimen (not shown) is gathered from the collection container, into scoop member 14. Sampler 2 is next inserted into container 1, so that sealing member 3 engages and seals open, upper end 16 of container 1, and so that scoop member 14 is located near the bottom 17 of container 1. If necessary, the apparatus may be tilted or turned to dislodge the sample from scoop member 14 so that it falls to the bottom 17 of container 1.

Downward pressure is exerted on push rod handle means 4, thereby compressing spring means 10 and moving piston means 7 downwardly to disengage scoop member 14 from housing 13. After scoop member 14 is released, the downward pressure is removed, and piston means 7 automatically moves upwardly to its normally uppermost rest position, as shown in FIG. 5.

Container 1 need not be reopened, and may be transported to a different location for examination.

In an alternative method, a portion of the specimen is gathered into scoop member 14 as described above. Sampler 2 is inserted into container 1, so that scoop member 14 is located near bottom 17, but without causing any sealing engagement between sealing member 3 and open, upper container end 16. As above, the contents of scoop member 14 are dislodged therefrom, so as to fall to the bottom 17 of container 1. Sampler 2 is then removed from container 1.

Scoop member 14 is disengaged as described above but outside the container, and separately disposed. Sampler 2 may be reintroduced into container 1 so that sealing member 3 engages and seals open, upper end 16 of container 1, thereby readying the apparatus for transport to a different location for examination.

The apparatus and method of this invention combine the features of ease of operation, convenience, and a relatively low risk of contamination to the person handling the sample.

The shape of the scoop member, housing, or container shown in the figures are illustrative, and do not limit the invention to the particular configurations set forth in the figures. Various modifications may be made without departing from the spirit and scope of the invention. Accordingly, the invention is not to be limited, except by the appended claims.

I have shown a convenient, sanitary, single-use apparatus and method for gathering and transporting biological samples, which product is disposable and economical to manufacture.

I claim:

1. A specimen gathering device comprising:
    an elongate housing having a bore therethrough, a first end, a second end, and a spring compression member disposed within said bore;
    a moveable piston means disposed within said bore having a proximal end disposed within said bore, and a spring engagement member located within said bore, said spring compression member being located between said proximal end and said spring engagement member;
    a push rod having a handle end extending exterior to said first end of said housing and a proximal end disposed within said bore and in contact with said piston means spring engagement member;
    a spring means in spring engagement with said spring management member and said spring compresion member urging said piston means toward said first end;
    an ejectable scoop member having a scoop end and an insert end, said insert end removably mounted within said second end so that said ejectable scoop member is removed from said second end when said piston is moved toward said second end and said proximal end forces said ejectable scoop member out of said second end; and
    a sealing member, sized to sealingly engage a preselected container having an open end, said sealing member fixed to the exterior of said elongate housing and oriented to seal said second end within said container.

2. The specimen gathering device of claim 1, including a container sized to fit said sealing member.

3. The specimen gathering device of claim 1, wherein the scoop end of said scoop member is spoon-shaped.

4. The specimen gathering device of claim 1, wherein said elongate housing, said moveable piston means, said spring compression member, and said ejectable scoop member are molded from plastics for disposable use.

5. The specimen gathering device of claim 1, wherein said sealing member is an annular member.

6. The specimen gathering device of claim 5, wherein said sealing member includes a shoulder to enhance the seal between it and said container.

7. The specimen gathering device of claim 1, wherein said elongate housing comprises two interlocking pieces.

8. The specimen gathering device of claim 7, wherein said moveable piston means spring engagement member is integrally connected to said push rod proximal end within said elongate housing.

9. The specimen gathering device of claim 8, wherein said spring compression member is located at a junction between the two interlocking pieces in said elongate housing.

10. A method for the sanitary collection of stool or other biological samples comprising:
    (a) collecting a portion of the sample in an ejectable scoop member held in a scoop member housing;
    (b) inserting the sample containing scoop member into a cylindrical container having an open end and a closed end;
    (c) dislodging the sample from the scoop member into the container; and
    (d) disengaging the ejectable scoop member from said scoop member housing.

11. The method of claim 10, wherein said ejectable scoop is disengaged from said scoop member housing after removal from said cylindrical container.

12. The method of claim 11, including the step of sealing said container for transport.

13. The method of claim 10, wherein said ejectable scoop member is disengaged from said scoop member housing within said cylindrical container.

14. The method of claim 13, including the step of sealing said open end of said cylindrical container with a sealing member mounted on the external surface of said scoop member housing.

15. The method of claim 13, including the step of transporting the sealed container.

* * * * *